United States Patent [19]

Esanu

[11] Patent Number: 4,569,938

[45] Date of Patent: Feb. 11, 1986

[54] DIURETIC, ANTIHYPERTENSIVE AND ANTIHISTAMINIC 7-CARBOXYMETHOXY-FURO-(3,4-C)-PYRIDINE DERIVATIVES

[75] Inventor: André Esanu, Paris, France

[73] Assignee: Societe de Conseils de Recherches et d'Applications Scientifiques, France

[21] Appl. No.: 668,394

[22] Filed: Nov. 5, 1984

[30] Foreign Application Priority Data

Nov. 17, 1983 [GB] United Kingdom ................ 8330658

[51] Int. Cl.[4] ................ A61K 31/435; C07D 491/048
[52] U.S. Cl. .................................... 514/302; 546/116
[58] Field of Search ........................ 546/116; 514/302

[56] References Cited

PUBLICATIONS

March, *Advanced Chemistry*, 2nd ed., McGraw-Hill, (1977), p. 357.
Morrison & Boyd, *Organic Chemistry*, 3rd ed., pp. 677, 556.
Garay et al., Stimulation of K+ Fluxes . . . Cells, Biochem. Pharmacol., vol. 33, No. 13, pp. 2013–2020, (1984).

*Primary Examiner*—Richard A. Schwartz
*Attorney, Agent, or Firm*—Lucas and Just

[57] ABSTRACT

This invention relates to new 1,3-dihydro-6-methyl-furo-(3,4-c)-pyridine derivatives of the general formula:

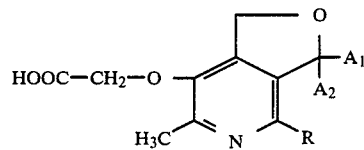

wherein, each of $A_1$ and $A_2$ represents various hydrocarbon groups, to pharmaceutically acceptable salts of them, to a process for the preparation of said derivatives from the corresponding 6-hydroxy compounds, treated by ethyl bromoacetate and then hydrolyzed. The invention further provides pharmaceutical compositions wherein said derivatives are used as active ingredients. The compounds are useful as diuretics, in lowering blood pressure and as antihistaminics.

5 Claims, No Drawings

DIURETIC, ANTIHYPERTENSIVE AND ANTIHISTAMINIC 7-CARBOXYMETHOXY-FURO-(3,4-C)-PYRIDINE DERIVATIVES

The invention relates to 7-carboxymethoxy-furo-(3,4-c)-pyridine derivatives and to a process for their preparation and to pharmaceutical compositions containing them.

The invention provides 1,3-dihydro-6-methyl-furo-(3,4-c)-pyridine derivatives of the general formula I:

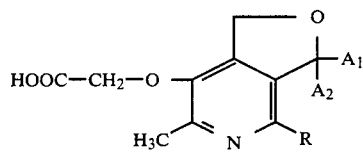

wherein each of $A_1$ and $A_2$ independently represents a hydrogen atom, a straight chain saturated or unsaturated hydrocarbon group having from 1 to 5 carbon atoms, a heterocyclic group having up to 6 ring atoms, a carbomonocyclic group, a phenylalkyl group or a phenylalkenyl group, each of the groups represented by $A_1$ and $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl groups has from 1 to 5 carbon atoms, dialkylaminoalkoxy groups in which each of the two alkyl groups and the alkoxy group has from 1 to 5 carbon atoms or α- or β-alkoxy-N-pyrrolidinyl groups in which the alkoxy group has from 1 to 5 carbon atoms and R represents a hydrogen or halogen atom; and further provides pharmaceutically acceptable salts of such compounds.

The compounds according to the invention are of interest for their therapeutic activity, principally in the fields of diuresis, the lowering of blood pressure and kidney protection, and as anti-histaminic agents.

The invention further provides a process for the preparation of 1,3-dihydro-6-methyl-furo-(3,4-c)-pyridine derivatives of the general formula I as defined above, the process comprising treating a compound of the general formula II

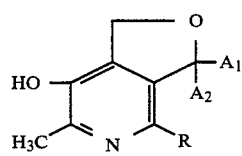

wherein $A_1$, $A_2$, and R have the meanings ascribed to them above with ethyl bromoacetate at 10°-70° C., in the presence of dimethylformamide and hydrolysing the resultant ester with sodium hydroxide.

The starting compounds II may be prepared as described in our U.S. Pat. No. 4,383,998 of 17.05.83.

The invention also provides a pharmaceutical composition comprising a 1,3-dihydro-6-methyl-furo-(3,4-c)-pyridine derivative of the general formula I as defined above or a pharmaceutically acceptable salt of such a compound in admixture with a pharmaceutically acceptable diluent or carrier.

The invention is illustrated by the following examples.

EXAMPLE 1

1,3-dihydro-3-ethyl-6-methyl-7-carboxymethoxy-furo-(3,4-c)-pyridine

Into a two liter reactor fitted with warming, cooling and stirring means, there was poured 300 ml of dried dimethylformamide, 4.8 g of sodium hydride, and slowly, under stirring, 38.1 g (0.1 mole) of 1,3-dihydro-3-ethyl-6-methyl-7-hydroxy-furo-(3,4-c)-pyridine. The temperature was raised to 40° C. and the mixture was stirred at that temperature for one hour. There was then added slowly, at 20° C., 11.4 ml (0.11 mole) of ethyl bromoacetate. Stirring was carried out for six hours, after which the reaction mixture was evaporated to dryness. The residue was taken up in dichloromethane, washed with water, reprecipitated, filtered off, dried and recrystallized from petroleum ether. The yield was 21 g (79%) of a white crystalline product, elemental analysis of which showed good correspondence with the formula $C_{14}H_{19}NO_4$ (i.e. the ethyl ester of the title compound).

The ester thus obtained—20 g (0.74 mole)—was treated in the same reactor with 100 ml of ethanol, 11 g (0.275 mole) of soda tablets and 200 ml of water, at reflux for two hours; after cooling, there was added dropwise, under stirring, 200 ml of 10% acetic acid and 100 ml of water, while maintaining the temperature below 20° C. The precipitate which appeared was separated off, washed twice with water, dried and recrystallized from a warm dissolution in mixture acetonitrile/methanol (50/50). There was thus obtained 10 g (yield 80%) of a white crystalline product, elemental analysis of which showed good correspondence with the formula $C_{12}H_{15}NO_4$. Melting point 212° C. (Tottoli).

EXAMPLE 2

1,3-dihydro-3-vinyl-3-p-thiomethylphenyl-6-methyl-7-carboxymethoxy-furo-(3,4-c)-pyridine This compound has been prepared by the method described in Example 1, from 1,3-dihydro-3-vinyl-3-p-thiomethylphenyl-6-methyl-7-hydroxy-furo-(3,4-c)-pyridine. The yield was 42% of a white crystalline product, elemental analysis of which showed good correspondence with the formula $C_{19}H_{19}NO_4S$. Melting point 191°-194° C.

EXAMPLE 3

1,3-dihydro-3-phenyl-6-methyl-7-carboxymethoxy-furo-(3,4-c)-pyridine

This compound has been prepared by the method described in Example 1, from 1,3-dihydro-3-phenyl-6-methyl-7-hydroxy-furo-(3,4-c)-pyridine. The yield was 67% of a white crystalline product, elemental analysis of which showed good correspondence with the formula $C_{16}H_{15}NO_4$. Melting point 220° C.

EXAMPLE 4

1,3-dihydro-3-p-chlorophenyl-6-methyl-7-carboxymethoxy-furo-(3,4-c)-pyridine

This compound has been prepared by the method described in Example 1, from 1,3-dihydro-3-p-chlorophenoxy-6-methyl-7-hydroxy-furo-(3,4-c)-pyridine.

The yield was 63% of a white crystalline product, elemental analysis of which showed good correspondence with the formula $C_{16}H_{14}NO_4Cl$. Melting point 226°–230° C.

EXAMPLE 5

1,3-dihydro-3-p-fluorophenyl-6-methyl-7-carboxymethoxy-furo-(3,4-c)-pyridine

This compound has been prepared by the method described in Example 1, from 1,3-dihydro-3-p-fluorophenyl-6-methyl-7-hydroxy-furo-(3,4-c)-pyridine. The yield was 47% of a white crystalline product, elemental analysis of which showed good correspondence with the formula $C_{16}H_{14}FNO_4$. Melting point 214° C.

EXAMPLE 6

1,3-dihydro-3-p-trifluoromethyl-phenyl-6-methyl-7-carboxymethoxy-furo-(3,4-c)-pyridine This compound has been prepared by the method described in Example 1, from 1,3-dihydro-3-p-trifluoromethyl-phenyl-6-methyl-7-hydroxy-furo-(3,4-c)-pyridine. The yield was 58% of a white crystalline product, elemental analysis of which showed good correspondence with the formula $C_{17}H_{14}F_3NO_4$. Melting point 200° C.

EXAMPLE 7

1,3-dihydro-3-p-(ethoxy-N-pyrrolidinyl)phenyl-6-methyl-7-carboxymethoxy-furo-(3,4-c)-pyridine This compound has been prepared by the method described in Example 1, from 1,3-dihydro-3-p-(ethoxy-N-pyrrolidinyl)-phenyl-6-methyl-7-hydroxy-furo-(3,4-c)-pyridine. The yield was 71% of a white crystalline product, elemental analysis of which showed good correspondence with the formula $C_{22}H_{26}N_2O_5$. Melting point 197° C.

EXAMPLE 8

1,3-dihydro-3-α-thienyl-6-methyl-7-carboxymethoxy-furo-(3,4-c)-pyridine

This compound has been prepared by the method described in Example 1, from 1,3-dihydro-3-α-thienyl-6-methyl-7-hydroxy-furo-(3,4-c)-pyridine. The yield was 73% of a pale beige crystalline product, elemental analysis of which showed good correspondence with the formula $C_{14}H_{13}NO_4S$. Melting point 172°–174° C.

EXAMPLE 9

1,3-dihydro-3-n-pentyl-3,6-dimethyl-7-carboxymethoxy-furo-(3,4-c)-pyridine

This compound has been prepared by the method described in Example 1, from 1,3-dihydro-3-n-pentyl-3,6-dimethyl-7-hydroxy-furo-(3,4-c)-pyridine. The yield was 76% of a white crystalline product, elemental analysis of which showed good correspondence with the formula $C_{16}H_{23}NO_4$. Melting point 211° C.

EXAMPLE 10

1,3-dihydro-3-p-chlorophenyl-3,6-dimethyl-7-carboxymethoxy-furo-(3,4-c)-pyridine This compound has been prepared by the method described in Example 1, from 1,3-dihydro-3-p-chlorophenyl-3,6-dimethyl-7-hydroxy-furo-(3,4-c)-pyridine. The yield was 61% of a crystalline product, the analysis of which showed acceptable correspondence with the formula $C_{17}H_{16}ClNO_4$. Melting point 184° C.

EXAMPLE 11

1,3-dihydro-3,6-dimethyl-3-p-chlorophenyl-7-carboxymethoxy-furo-(3,4-c)-pyridine This compound has been prepared by the method described in Example 1, from 1,3-dihydro-3,6-dimethyl-3-p-chlorophenyl-7-hydroxy-furo-(3,4-c)-pyridine. The yield was 43% of a white crystalline product, elemental analysis of which showed good correspondence with the formula $C_{17}H_{16}ClNO_4$. Melting point 201°–206° C.

EXAMPLE 12

1,3-dihydro-3-p-fluorophenyl-3,6-dimethyl-7-carboxymethoxy-furo-(3,4-c)-pyridine This compound has been prepared by the method described in Example 1, from 1,3-dihydro-3-p-fluorophenyl-3,6-dimethyl-7-hydroxy-furo-(3,4-c)-pyridine. The yield was 68% of a crystalline product, the analysis of which showed acceptable correspondence with the formula $C_{17}H_{16}FNO_4$. Melting point 184°–186° C.

EXAMPLE 13

1,3-dihydro-3-ethyl-3-n-butyl-6-methyl-7-carboxymethoxy-furo-(3,4-c)-pyridine

This compound has been prepared by the method described in Example 1, from 1,3-dihydro-3-ethyl-3-n-butyl-6-methyl-7-hydroxy-furo-(3,4-c)-pyridine. The yield was 78% of a white crystalline product, elemental analysis of which showed good correspondence with the formula $C_{16}H_{23}NO_4$. Melting point 193° C.

EXAMPLE 14

1,3-dihydro-3-ethyl-3-α-furyl-6-methyl-7-carboxymethoxy-furo-(3,4-c)-pyridine

This compound has been prepared by the method described in Example 1, from 1,3-dihydro-3-ethyl-3-α-furyl-6-methyl-7-hydroxy-furo-(3,4-c)-pyridine. The yield was 71% of a crystalline product, elemental analysis of which showed acceptable correspondence with the formula $C_{16}H_{17}NO_5$. Melting point 169° C.

EXAMPLE 15

1,3-dihydro-3-vinyl-3-p-methylthiophenyl-6-methyl-7-carboxymethoxy-furo-(3,4-c)-pyridine This compound has been prepared by the method described in Example 1, from 1,3-dihydro-3-vinyl-3-p-methylthiophenyl-6-methyl-7-hydroxy-furo-(3,4-c)-pyridine. The yield was 81% of a crystalline product, elemental analysis of which showed acceptable correspondence with the formula $C_{19}H_{19}NO_4S$. Melting point 191°–194° C.

EXAMPLE 16

1,3-dihydro-3-phenyl-3-p-toluyl-6-methyl-7-carboxymethoxy-furo-(3,4-c)-pyridine

This compound has been prepared by the method described in Example 1, from 1,3-dihydro-3-phenyl-3-p-toluyl-6-methyl-7-hydroxy-furo-(3,4-c)-pyridine. The yield was 57% of a white crystalline product, elemental analysis of which showed good correspondence with the formula $C_{23}H_{21}NO_4$. Melting point 223° C.

EXAMPLE 17

1,3-dihydro-3-α-furyl-3-p-methylthiophenyl-6-methyl-7-carboxymethoxy-furo-(3,4-c)-pyridine This compound has been prepared by the method described in Example 1, from 1,3-dihydro-3-α-furyl-3-p-methylthiophenyl-6-methyl-7-hydroxy-furo-(3,4-c)-pyridine. The yield was 43% of a crystalline product, elemental analysis of which showed good correspondence with the formula $C_{21}H_{19}NO_5S$. Melting point 139° C.

For the 4-bromo or chloro 7-carboxymethoxy derivatives, the detailed preparations will not be repeated. Only the name of each compound, the name of the corresponding starting material, the yield, the formula and the melting point will be given.

EXAMPLE 18

1,3-dihydro-3-ethyl-4-chloro-6-methyl-7-carboxymethoxy-furo-(3,4-c)-pyridine

From 1,3-dihydro-3-ethyl-4-chloro-6-methyl-7-hydroxy-furo-(3,4-c)-pyridine:

Yield 55%; Formula $C_{13}H_{16}ClNO_4$; Melting point 181° C.

EXAMPLE 19

1,3-dihydro-3-n-butyl-4-chloro-6-methyl-7-carboxymethyl-furo-(3,4-c)-pyridine

From 1,3-dihydro-3-n-butyl-4-chloro-6-methyl-7-hydroxy-furo-(3,4-c)-pyridine:

Yield 58%; Formula $C_{13}H_{20}ClNO_4$; Melting point 170° C.

EXAMPLE 20

1,3-dihydro-3-p-chlorophenyl-4-bromo-6-methyl-7-carboxymethoxy-furo-(3,4-c)-pyridine From 1,3-dihydro-3-p-chlorophenyl-4-bromo-6-methyl-7-hydroxy-furo-(3,4-c)-pyridine:

Yield 53%; Formula $C_{16}H_{13}BrClNO_4$; Melting point 194°–196° C.

EXAMPLE 21

1,3-dihydro-3-m-trifluoromethylphenyl-4-bromo-6-methyl-7-carboxymethoxy-furo-(3,4-c)-pyridine From 1,3-dihydro-3-m-trifluoromethylphenyl-4-bromo-6-methyl-7-hydroxy-furo-(3,4-c)-pyridine:

Yield 43%; Formula $C_{17}H_{13}BrF_3NO_4$; Melting point 207°–209° C.

EXAMPLE 22

1,3-dihydro-3-p-methoxyphenyl-4-chloro-6-methyl-7-carboxymethoxy-furo-(3,4-c)-pyridine From 1,3-dihydro-3-p-methoxyphenyl-4-bromo-6-methyl-7-hydroxy-furo-(3,4-c)-pyridine:

Yield 48%; Formula $C_{17}H_{16}ClNO_5$; Melting point 178° C.

EXAMPLE 23

1,3-dihydro-3-p-methylthiophenyl-4-bromo-6-methyl-7-carboxymethoxy-furo-(3,4-c)-pyridine From 1,3-dihydro-3-p-methylthiophenyl-4-bromo-6-methyl-7-hydroxy-furo-(3,4-c)-pyridine:

Yield 38%; Formula $C_{17}H_{16}BrNO_4S$; Melting point 157°–159° C.

EXAMPLE 24

1,3-dihydro-3-α-thienyl-4-chloro-6-methyl-7-carboxymethoxy-furo-(3,4-c)-pyridine From 1,3-dihydro-3-α-thienyl-4-chloro-6-methyl-7-hydroxy-furo-(3,4-c)-pyridine:

Yield 35%; Formula $C_{14}H_{12}ClNO_4S$; Melting point 149°–151° C.

EXAMPLE 25

1,3-dihydro-3,3,6-trimethyl-4-chloro-7-carboxymethoxy-furo-(3,4-c)-pyridine

From 1,3-dihydro-3,3,6-trimethyl-4-chloro-7-hydroxy-furo-(3,4-c)-pyridine:

Yield 51%; Formula $C_{12}H_{14}ClNO_4$; Melting point 192° C.

EXAMPLE 26

1,3-dihydro-3-phenyl-3,6-dimethyl-4-chloro-7-carboxymethoxy-furo-(3,4-c)-pyridine From 1,3-dihydro-3-phenyl-3,6-dimethyl-4-chloro-7-hydroxy-furo-(3,4-c)-pyridine:

Yield 47%; Formula $C_{17}H_{16}ClNO_4$; Melting point 181°–183° C.

EXAMPLE 27

1,3-dihydro-3-p-chlorophenyl-3,6-dimethyl-4-bromo-7-carboxymethoxy-furo-(3,4-c)-pyridine From 1,3-dihydro-3-p-chlorophenyl-3,6-dimethyl-4-bromo-7-hydroxy-furo-(3,4-c)-pyridine:

Yield 46%; Formula $C_{17}H_{15}BrClNO_4$; Melting point 180°–182° C.

EXAMPLE 28

1,3-dihydro-3-α-thienyl-3,6-dimethyl-4-bromo-7-carboxymethoxy-furo-(3,4-c)-pyridine From 1,3-dihydro-3-α-thienyl-3,6-dimethyl-4-bromo-7-hydroxy-furo-(3,4-c)-pyridine:

Yield 36%; Formula $C_{15}H_{14}BrNO_4S$; Melting point 163°–165° C.

EXAMPLE 29

1,3-dihydro-3-ethyl-3-p-chlorophenyl-4-bromo-6-methyl-7-carboxymethoxy-furo-(3,4-c)-pyridine From 1,3-dihydro-3-ethyl-3-p-chlorophenyl-4-bromo-6-methyl-7-hydroxy-furo-(3,4-c)-pyridine:

Yield 38%; Formula $C_{18}H_{17}BrClNO_4$; Melting point 135°–138° C.

EXAMPLE 30

1,3-dihydro-3-propyl-3-p-chlorophenyl-4-bromo-6-methyl-7-carboxymethoxy-furo-(3,4-c)-pyridine From 1,3-dihydro-3-propyl-3-p-chlorophenyl-4-bromo-6-methyl-7-hydroxy-furo-(3,4-c)-pyridine:

Yield 41%; Formula $C_{19}H_{19}BrClNO_4$; Melting point 130° C.

EXAMPLE 31

1,3-dihydro-3-p-diethylaminoethoxyphenyl-3-phenyl-4-chloro-6-methyl-7-carboxymethoxy-furo-(3,4-c)-pyridine From 1,3-dihydro-3-p-diethylaminoethoxyphenyl-3-phenyl-4-chloro-6-methyl-7-hydroxy-furo-(3,4-c)-pyridine:

Yield 33%; Formula $C_{27}H_{29}ClN_2O_5$; Melting point 143°–146° C.

EXAMPLE 32

1,3-dihydro-3,3-di(p-chlorophenyl)-4-chloro-6-methyl-7-carboxymethoxy-furo-(3,4-c)-pyridine From 1,3-dihydro-3,3-di(p-chlorophenyl)-4-chloro-6-methyl-7-hydroxy-furo-(3,4-c)-pyridine:

Yield 44%; Formula $C_{22}H_{16}Cl_3NO_4$; Melting point 126°–128° C.

TOXICITY $DL_{50}$ was determined per os and IP on mice. According to the compounds, it comprised between 0.8 to over 2 g/kg (per os) and 0.45 to 1.35 g/kg IP.

PHARMACOLOGY

A complete pharmacological experimentation was conducted and the following tests are reported below.

A—Passive cutaneous anaphylaxy

This experiment was conducted as described in Fiche Technique no. 48 of J.Pharm. Paris 1979 10 (1) pages 69–72.

Male Sprague-Dowley rats (180–200 g) received two intra-dermal injections of immunserum in the back; 72 hours later, they received a IV (penis vein) injection of 1 ml of a mixture of ovalbumine (5 mg/ml) and Evans blue (2.5 mg/ml): this induced the formation of wheals around the places of injection of immunserum. Wheals were taken 30 minutes after this formation, measured then incubated for 24 hours at 65° C. in 4 ml of formamide (for extracting the Evans blue). Optical density of the supernatant was determined at 620 nm by a spectrophotometer.

A first batch of 8 rats was used for control; a second batch (8) was used for treatment by a reference compound (theophylline, 25 mg/kg) and ten other batches (all of 8 rats) were used for the treatment by 10 of the compounds of the present invention (all at 25 mg/kg) identified by their example number; for these eleven batches, the appropriate compound was administered per os, one hour before the injection of ovalbumine/Evans blue mixture. The percentage of wheals reduction, in surface and in colour, was determined by comparison with the control. The results are reported on the left part of following table.

B—Anti-histaminic action

This experiment was conducted as described by Doepfner W. and Cerletti A., Int. Arch. Allergy 12, 89 1958 and J. Pharmac. and exp. Ther. (1974) 191 (2) pages 300–310.

Male Sprague-Dowley rats (140–160 g) were submitted to hydric fast for 18 hours before receiving 1 ml/kg of water (for control), 0.2 of an aqueous solution or suspension of experimented compounds. The volume of the left posterior paw was measured by plethysmography, then 0.1 ml of 5% histamine hydrochloride was injected. The inflammatory response was evaluated by a subsequent volume determination one hour later.

Batches of each 8 animals were used: one for control, ten for tested compounds (the same as in A above) and two for reference compounds mequitazine and promethazine, all at the dose of 25 mg/kg. The percentage of reduction of inflammatory response was obtained by comparison with control. The results are reported in the right part of the following table.

From these two experiments, it clearly appears that the compounds of the invention present a strong antihistaminic action.

PRESENTATION-POSOLOGY

For human use by oral route, tablets or gelatine capsules containing 0.25 g of a compound according to the invention are preferred. By IV route, phials containing the same amount, to be injected with a perfusion are retained. Daily does in human therapy are from 0.25 to 2 g per os 02 0.25 to 1 g, IV.

| Compounds | % of wheals reduction | | Histamine induced Oedema % of inflammatory reduction |
|---|---|---|---|
| | Surface | Colour | |
| Theophylline | −63 | −61 | |
| Ex 1 | −49 | −56 | −80 |
| Ex 3 | −61 | −62 | −58 |
| Ex 4 | −53 | −64 | −54 |
| Ex 5 | −56 | −81 | −48 |
| Ex 8 | −49 | −60 | −67 |
| Ex 11 | −44 | −47 | −77 |
| Ex 12 | −60 | −66 | −64 |
| Ex 15 | −76 | −85 | −37 |
| Ex 20 | −59 | −63 | −55 |
| Ex 27 | −48 | −56 | −66 |
| Mequitazine | | | −61 |
| Promethazine | | | −39 |

I claim:

1. A 1,3-dihydro-6-methyl-furo(3,4-c)-pyridine derivative of the formula:

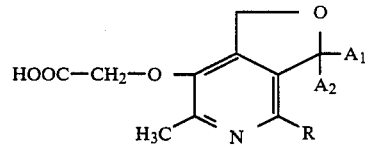

wherein each of $A_1$ and $A_2$ independently represents a hydrogen atom, a straight chain saturated or unsaturated hydrocarbon group having from 1 to 5 carbon atoms, a heterocyclic group which is an unsaturated 5-membered ring wherein the heteroatom is oxygen or sulfur, a phenyl group, a phenylloweralkyl group or a phenylloweralkenyl group, each of the groups represented by $A_1$ and $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or α- or β-alkoxy-N-pyrrolidinyl groups in which the alkoxy group has from 1 to 5 carbon atoms and R represents a hydrogen or halogen atom; or a pharmaceutically acceptable salt of such a compound.

2. A pharmaceutical composition comprising as an active agent therein an amount of a 1,3-dihydro-6-methyl-furo-(3,4-c)-pyridine derivative of the formula:

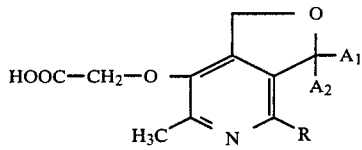

wherein
each of $A_1$ and $A_2$ independently represents a hydrogen atom, a straight chain saturated or unsaturated hydrocarbon group having from 1 to 5 carbon atoms, a heterocyclic group which is an unsaturated 5-membered ring wherein the heteroatom is oxygen or sulfur, a phenyl group, a phenylloweralkyl group or a phenylloweralkenyl group, each of the groups represented by $A_1$ and $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or α- or β-alkoxy-N-pyrrolidinyl groups in which the alkoxy group has from 1 to 5 carbon atoms and R represents a hydrogen or halogen atom; or a pharmaceutically acceptable salt of such a compound in admixture with a pharmaceutically acceptable diluent or carrier, said amount being effective to act as a diuretic, to lower blood pressure or to act as an antihistaminic agent.

3. A method of achieving diuresis in a host in need thereof comprising the administration of a diuretically effective amount of a 1,3-dihydro-6-methyl-furo-(3,4-c)-pyridine derivative of the formula:

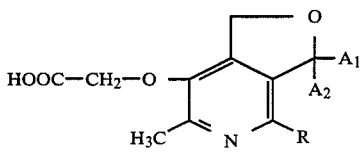

wherein
each of $A_1$ and $A_2$ independently represents a hydrogen atom, a straight chain saturated or unsaturated hydrocarbon group having from 1 to 5 carbon atoms, a heterocyclic group which is an unsaturated 5-membered ring wherein the heteroatom is oxygen or sulfur, a phenyl group, a phenylloweralkyl group or a phenylloweralkenyl group, each of the groups represented by $A_1$ and $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or α- or β-alkoxy-N-pyrrolidinyl groups in which the alkoxy group has from 1 to 5 carbon atoms and R represents a hydrogen or halogen atom; or a pharmaceutically acceptable salt of such a compound in admixture with a pharmaceutically acceptable diluent or carrier.

4. A method of lowering blood pressure in a host in need thereof comprising the administration of a blood pressure lowering amount of a 1,3-dihydro-6-methyl-furo-(3,4-c)-pyridine derivative of the formula:

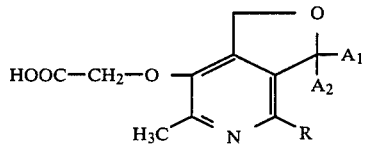

wherein
each of $A_1$ and $A_2$ independently represents a hydrogen atom, a straight chain saturated or unsaturated hydrocarbon group having from 1 to 5 carbon atoms, a heterocyclic group which is an unsaturated 5-membered ring wherein the heteroatom is oxygen or sulfur, a phenyl group, a phenylloweralkyl group or a phenylloweralkenyl group, each of the groups represented by $A_1$ and $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or α- or β-alkoxy-N-pyrrolidinyl groups in which the alkoxy group has from 1 to 5 carbon atoms and R represents a hydrogen or halogen atom; or a pharmaceutically acceptable salt of such a compound in admixture with a pharmaceutically acceptable diluent or carrier.

5. A method of treating histaminic reaction in a host in need thereof comprising the administration of an antihistaminic amount of a 1,3-dihydro-6-methyl-furo-(3,4-c)-pyridine derivative of the formula:

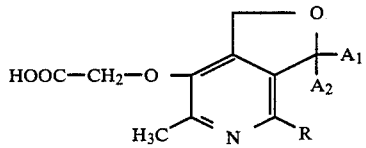

wherein
each of $A_1$ and $A_2$ independently represents a hydrogen atom, a straight chain saturated or unsaturated hydrocarbon group having from 1 to 5 carbon atoms, a heterocyclic group which is an unsaturated 5-membered ring wherein the heteroatom is oxygen or sulfur, a phenyl group, a phenylloweralkyl group or a phenylloweralkenyl group, each of the groups represented by $A_1$ and $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or α- or β-alkoxy-N-pyrrolidinyl groups in which the alkoxy group has from 1 to 5 carbon atoms and R represents a hydrogen or halogen atom; or a pharmaceutically acceptable salt of such a compound in admixture with a pharmaceutically acceptable diluent or carrier.

* * * * *

UNITED STATES PATENT AND TRADEMARK OFFICE
CERTIFICATE OF CORRECTION

PATENT NO.   :   4,569,938

DATED        :   February 11, 1986

INVENTOR(S)  :   Andre Esanu

It is certified that error appears in the above-identified patent and that said Letters Patent is hereby corrected as shown below:

Column 8, line 14, change "02 0.25 to 1 g, IV" to --or 0.25 to 1 g, IV--.

Signed and Sealed this

Twelfth Day of August 1986

[SEAL]

Attest:

Attesting Officer

DONALD J. QUIGG

Commissioner of Patents and Trademarks